US012758556B2

(12) United States Patent
Gendelman et al.

(10) Patent No.: US 12,758,556 B2
(45) Date of Patent: Oct. 13, 2026

(54) COMPOSITIONS AND METHODS FOR THE DELIVERY OF THERAPEUTICS

(71) Applicant: Board of Regents of the University of Nebraska, Lincoln, NE (US)

(72) Inventors: Howard E. Gendelman, Omaha, NE (US); Xin-Ming Liu, Omaha, NE (US); Benson Edagwa, Omaha, NE (US)

(73) Assignee: Board of Regents of The University of Nebraska, Lincoln, NE (US)

( * ) Notice: Subject to any disclaimer, the term of this patent is extended or adjusted under 35 U.S.C. 154(b) by 1156 days.

(21) Appl. No.: 17/655,112

(22) Filed: Mar. 16, 2022

(65) Prior Publication Data

US 2022/0211714 A1 Jul. 7, 2022

Related U.S. Application Data

(63) Continuation of application No. 15/517,581, filed as application No. PCT/US2015/054826 on Oct. 9, 2015, now Pat. No. 11,311,545.

(60) Provisional application No. 62/061,759, filed on Oct. 9, 2014.

(51) Int. Cl.

| | |
|---|---|
| ***A61K 31/52*** | (2006.01) |
| ***A61K 9/00*** | (2006.01) |
| ***A61K 9/51*** | (2006.01) |
| ***A61K 31/513*** | (2006.01) |
| ***A61K 47/54*** | (2017.01) |
| ***A61K 47/55*** | (2017.01) |
| ***A61K 47/64*** | (2017.01) |
| ***A61K 47/69*** | (2017.01) |
| ***C07D 411/04*** | (2006.01) |
| ***C07D 473/16*** | (2006.01) |

(52) U.S. Cl.

CPC ............ *A61K 31/52* (2013.01); *A61K 9/0019* (2013.01); *A61K 9/5146* (2013.01); *A61K 31/513* (2013.01); *A61K 47/542* (2017.08); *A61K 47/551* (2017.08); *A61K 47/64* (2017.08); *A61K 47/6901* (2017.08); *A61K 47/6907* (2017.08); *A61K 47/6921* (2017.08); *A61K 47/6929* (2017.08); *C07D 411/04* (2013.01); *C07D 473/16* (2013.01)

(58) Field of Classification Search

CPC ................ A61K 31/52; A61K 47/6907; A61K 47/6929; A61K 47/542; A61K 47/551; A61K 47/64; A61K 47/6901; A61K 47/6921; A61K 9/0019; A61K 9/5146; A61K 31/513; C07D 411/04; C07D 473/16

See application file for complete search history.

(56) References Cited

U.S. PATENT DOCUMENTS

| | | | | |
|---|---|---|---|---|
| 5,049,671 | A * | 9/1991 | Daluge ................ | C07D 239/48 544/324 |
| 5,145,684 | A | 9/1992 | Liversidge et al. | |
| 6,045,829 | A | 4/2000 | Liversidge et al. | |
| 6,068,858 | A | 5/2000 | Liversidge et al. | |
| 6,835,396 | B2 | 12/2004 | Brynjelsen et al. | |
| 7,112,340 | B2 | 9/2006 | Kipp et al. | |
| 9,808,428 | B2 | 11/2017 | Gendelman et al. | |
| 11,311,545 | B2 | 4/2022 | Gendelman et al. | |
| 2002/0041898 | A1 | 4/2002 | Unger et al. | |
| 2004/0138157 | A1 | 7/2004 | Walker | |
| 2005/0048002 | A1 | 3/2005 | Rabinow et al. | |
| 2006/0280430 | A1 | 12/2006 | Rabinow et al. | |
| 2007/0003608 | A1 | 1/2007 | Almond et al. | |
| 2007/0042988 | A1 | 2/2007 | Klumpp et al. | |
| 2008/0241256 | A1 | 10/2008 | Kuhn | |
| 2009/0274765 | A1 | 11/2009 | Beduneau et al. | |
| 2011/0039798 | A1 | 2/2011 | Doncel et al. | |
| 2011/0085987 | A1 | 4/2011 | Wang et al. | |
| 2012/0202823 | A1 | 8/2012 | Zeidan et al. | |
| 2013/0236553 | A1 | 9/2013 | Gendelman et al. | |
| 2013/0244966 | A1 | 9/2013 | Milne et al. | |
| 2014/0017330 | A1 | 1/2014 | Vinogradov | |
| 2014/0099283 | A1 | 4/2014 | Gosselin et al. | |
| 2014/0323425 | A1 | 10/2014 | Calvez et al. | |
| 2015/0297587 | A1 | 10/2015 | Gelbard et al. | |
| 2017/0304308 | A1 | 10/2017 | Gendelman et al. | |

FOREIGN PATENT DOCUMENTS

| | | | |
|---|---|---|---|
| EP | 0349242 | A2 | 1/1990 |
| EP | 2682397 | A1 | 1/2014 |
| JP | H04295420 | A | 10/1992 |
| WO | WO-9902665 | A1 | 1/1999 |
| WO | WO-2000066090 | A1 | 11/2000 |
| WO | WO-02087424 | A2 | 11/2002 |
| WO | WO-2004069812 | A1 | 8/2004 |
| WO | WO-2005072706 | A2 | 8/2005 |
| WO | WO-2006116764 | A1 | 11/2006 |
| WO | WO-2007095269 | A2 | 8/2007 |

(Continued)

OTHER PUBLICATIONS

U.S. Appl. No. 15/517,581, filed Apr. 7, 2017, U.S. Pat. No. 11,311,545, Apr. 26, 2022, Issued.

(Continued)

*Primary Examiner* — James H Alstrum-Acevedo
*Assistant Examiner* — Manahil Mirghani Ali Abdalhameed
(74) *Attorney, Agent, or Firm* — Fenwick & West LLP; Matthew Pavao; Robert Powers

(57) ABSTRACT

The present invention provides compositions and methods for the delivery of antivirals to a cell or subject.

20 Claims, 6 Drawing Sheets

(56) References Cited

FOREIGN PATENT DOCUMENTS

Figure 1:
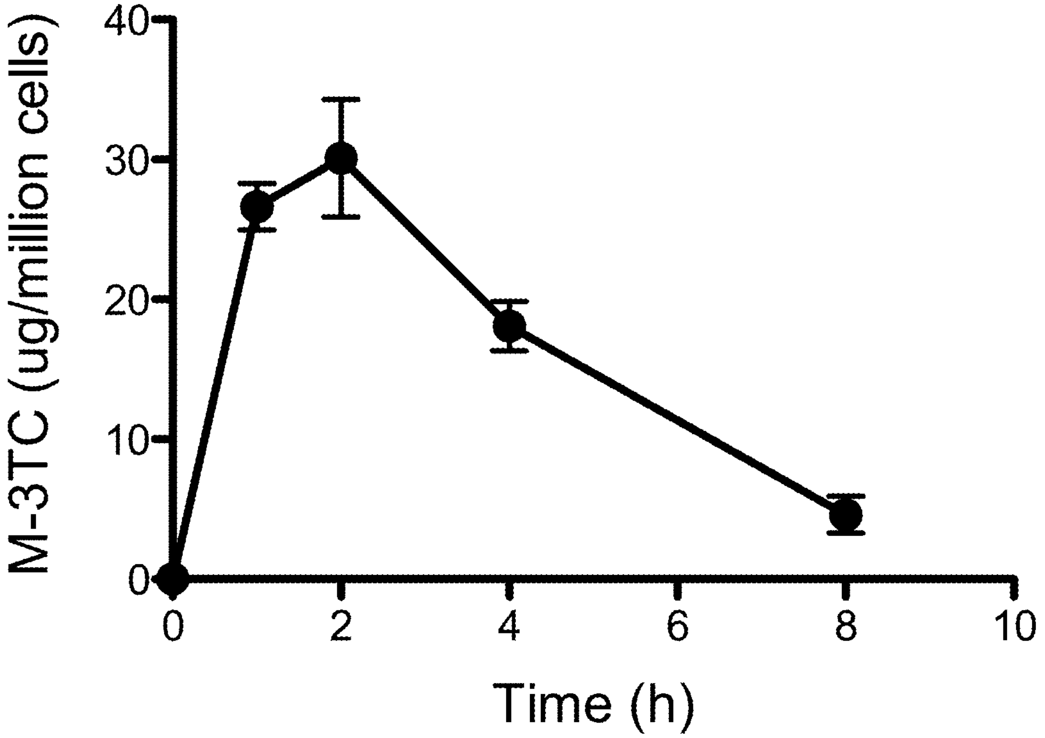

| | | | |
|---|---|---|---|
| WO | WO-2009051837 | A2 | 4/2009 |
| WO | WO-2010009075 | A1 | 1/2010 |
| WO | WO-2010011814 | A1 | 1/2010 |
| WO | WO-2011119566 | A1 | 9/2011 |
| WO | WO-2012037320 | A2 | 3/2012 |
| WO | WO-2012061480 | A2 | 5/2012 |
| WO | WO-20120158811 | A2 | 11/2012 |
| WO | WO-2013158549 | A1 | 10/2013 |
| WO | WO-2014085795 | A1 | 6/2014 |
| WO | WO-2014169207 | A1 | 10/2014 |
| WO | WO-2015108945 | A2 | 7/2015 |
| WO | WO-2015127437 | A1 | 8/2015 |
| WO | WO-2016057866 | A1 | 4/2016 |
| WO | WO-2016099982 | A2 | 6/2016 |
| WO | WO-20170223280 | A2 | 12/2017 |
| WO | WO-20190140365 | A1 | 7/2019 |
| WO | WO-2019199756 | A1 | 10/2019 |

OTHER PUBLICATIONS

U.S. Appl. No. 16/772,995, filed Jun. 15, 2020, Pending.
U.S. Appl. No. 16/981,325, filed Sep. 16, 2020, Pending.
Agarwal, A.G., et al., Synthesis and biological evaluation of fatty acyl ester derivatives of (−)-2',3'-dideoxy-3'-thiacytidine, J Med Chem, 55(10): 4861-4871 (2012).
Arainga, M., et al., Opposing regulation of endolysosomal pathways by long-acting nanoformulated antiretroviral therapy and HIV-1 in human macrophages, Retrovirology, 12: 5 (2015).
Baert, L., et al., Development of a long-acting injectable formulation with nanoparticles of rilpivirine (TMC278) for HIV treatment, Eur J Pharm Biopharm, 72(3): 502-508 (2009).
Balkundi, S., et al., Comparative manufacture and cell-based delivery of antiretroviral nanoformulations, Int J Nanomedicine, 6: 3393-3404 (2011).
Batrakova, E.V., et al., Cell-mediated drugs delivery, Expert Opin Drug Deliv, 8(4): 415-433 (2011).
Bhatia, M., et al., Nanoparticle technology for the delivery of poorly water-soluble drug, Pharm Tech, 30(2): 82-92 (2006).
Chattopadhyay, N., et al., Solid lipid nanoparticles enhance the delivery of the HIV protease inhibitor, atazanavir, by a human brain endothelial cell line, Pharm Res, 25(10): 2262-2271 (2008).
Edagwa, B.J., et al., Development of HIV reservoir targeted long acting nanoformulated antiretroviral therapies, Curr Med Chem, 21(36): 4186-4198 (2014).
Edagwa, B.J., et al., Long-acting antituberculous therapeutic nanoparticles target macrophage endosomes, FASEB J, 28(12): 5071-5082 (2014).
Gautam, N., et al., Pharmacokinetics, biodistribution, and toxicity of folic acid-coated antiretroviral nanoformulations, Antimicrob Agents Chemother, 58(12): 7510-7519 (2014).
Gautam, N., et al., Preclinical pharmacokinetics and tissue distribution of long-acting nanoformulated antiretroviral therapy, Antimicrob Agents Chemother, 57(7): 3110-3120 (2013).
Gavegnano, C., et al., Antiretroviral therapy in macrophages: implication for HIV eradication. Antivir Chem Chemother, 20(2): 63-78 (2009).
Guo, D., et al., Creation of a long-acting nanoformulated 2',3'-dideoxy-3'-thiacytidine, J Acquir Immune Defic Syndr, 74(3): e75-e83 (2017).
Guo, D., et al., Endosomal trafficking of nanoformulated antiretroviral therapy facilitates drug particle carriage and HIV clearance, J Virol, 88(17): 9504-9513 (2014).
Jain, S.K., et al., Mannosylated gelatin nanoparticles bearing an anti-HIV drug didanosine for site-specific delivery, Nanomedicine, 4(1): 41-48 (2008).
Kanmogne, G.D., et al., Mononuclear phagocyte intercellular crosstalk facilitates transmission of cell-targeted nanoformulated atiretroviral drugs to human brain endothelial cells, Int J Nanomedicine, 7: 2373-2388 (2012).
Kinman, L., et al., Optimization of lipid-indinavir complexes for localization in lymphoid tissues of HIV-infected macaques, J Acquir Immune Defic Sundr, 42(2): 155-161 (2006).
Law, D., et al., Physicochemical considerations in the preparation of amorphous ritonavir-poly(ethylene glycol) 8000 solid dispersions, J Pharm Sci, 90(8): 1015-1025 (2001).
Li, Q., et al., Synthesis of lamivudine stearate and antiviral activity of stearic acid-g-chitosan oligosaccharide polymeric micelles delivery system, Eur J Pharm Sci, 41(3-4): 498-507 (2010).
Lin, Z., et al., ProTide generated long-acting abacavir nanoformulations, Chem Commun (Cambridge), 54(60): 8371-8374 (2018).
Liu, F., et al., Targeted cancer therapy with novel high drug-loading nanocrystals, J Pharm Sci, 99(8): 3542-3551 (2010).
Low, P.S., et al., Discovery and development of folic-acid-based receptor targeting for imaging and therapy of cancer and inflammatory diseases, Acc Chem Res, 41(1): 120-129 (2008).
McGuigan, C., et al., The application of phosphoramidate ProTide technology to the potent anti-HCV compound 4'-azidocytidine (R1479), Bioorg Med Chem Lett, 19(15): 4250-4254 (2009).
Moghimi, S.M., et al., Poloxamers and poloxamines in nanoparticle engineering and experimental medicine, Trends Biotechnol, 18(10): 412-420 (2000).
Nowacek, A.S., Development of a macrophage-mediated delivery system for crystalline antiretroviral nanoparticles, Dissertation, University of Nebraska, 219 pages (2011).
Nowacek, A.S., et al., NanoART synthesis, characterization, uptake, release and toxicology for human monocyte-macrophage drug delivery, Nanomedicine (Lond.), 4(8): 903-917 (2009).
Nowacek, A.S., et al., Nanoformulated antiretroviral Combinations extend drug release and antiretroviral responses in HIV-1 infected macrophages: Implications for neuroAIDS therapeutics, J Neuroimmune Pharmacol, 5(4): 592-601 (2010).
PCT/US2015/054826 International Search Report and Written Opinion mailed Jan. 7, 2016.
PCT/US2019/013462 International Search Report and Written Opinion mailed Mar. 5, 2019.
Puligujja, P., et al., Macrophage Folate Receptor-Targeted Antiretroviral Therapy Facilitates Drug Entry, Retention, Antiretroviral Activities and Biodistribution for Reduction of Human Immunodeficiency Virus Infections, Nanomedicine, 9(8): 1263-1273 (2013).
Puligujja, P., et al., Pharmacodynamics of long-acting folic acid-receptor targeted ritonavir-boosted atazanavir nanoformulations, Biomaterials, 41: 141-150 (2015).
Rowe, R.C., et al., Handbook of Pharmaceutical Excipients, 6th Edition, Pharmaceutical Press, pp. 317-324 (2009).
The essential chemical industry—online, pp. 1-8, (2013) retrieved on Feb. 8, 2018 from <http://www.essentialchemical industry.ord/materials-and-applications/surfactants.html>.
The Merck Index Online entries for "Atazanavir" (monograph M2119), "Idinavir" (monograph M6253), and "Ritonavir" (monograph M9636), 5 pages (2013).
Thomas, T.P., et al., Folate-targeted nanoparticles show efficacy in the treatment of inflammatory arthritis, Arthritis Rheum, 63(9): 2671-2680 (2011).
Xia, W., et al., A functional folate receptor is induced during macrophage activation and can be used to target drugs to activated macrophages, Blood, 113(2): 438-446 (2009).
U.S. Appl. No. 15/517,581, filed Apr. 7, 2017, Allowed.
Dobrowska-Mas, E., Insights on fatty acids in lipophlic prodrug strategy, IRJPAC, 14(4): 1-10 (2017).
Guarino, V.R., et al., Prodrugs of amides, imides and other NH-acidic compounds in Prodrugs: Challenges and Rewards Part 1, p. 24, American Association of Pharmaceutical Sciences, New York, pp. 134-187 (2007).
Huang, B., et al., First discovery of a potential carbonate prodrug of NNRTI drug candidate RDEA427 with submicromolar inhibitory activity against HIV-1 K103N/Y181C double mutant strain, Bioorg Med Chem Lett, 28(8): 1348-1351 (2018).
Irby, D., et al., Lipid-drug conjugate for enhancing drug delivery, Mol Pharm, 14(5): 1325-1338 (2017).
Krise, J.P., et al., Prodrugs of Amines in Prodrugs: Challenges and Rewards Part 1, American Association of Pharmaceutical Sciences, New York, pp. 102-131 (2007).

(56) References Cited

OTHER PUBLICATIONS

Namasivayam, V., et al., The Journey of HIV-1 non-nucleoside reverse transcriptase inhibitors (NNRTIs) from lab to clinic, J Med Chem, 62(10): 4851-4883 (2019).
PCT/US2019/026497 International Search Report and Written Opinion mailed Jun. 18, 2019.
Rohde, M., et al., Biological conversion of aripiprazole lauroxil—An N-acyloxymethyl aripiprazole prodrug, Results Pharma Sci, 4: 19-25 (2014).

* cited by examiner

Inguinal lymph nodes

Peritoneal macrophages

Spleen

COMPOSITIONS AND METHODS FOR THE DELIVERY OF THERAPEUTICS

This application is a continuation of U.S. application Ser. No. 15/517,581 filed Apr. 7, 2017, now issued as U.S. Pat. No. 11,311,545 on Apr. 26, 2022, which is a § 371 application of PCT/US2015/054826, filed Oct. 9, 2015, which claims priority under 35 U.S.C. § 119 (e) to U.S. Provisional Patent Application No. 62/061,759, filed Oct. 9, 2014. The foregoing applications are incorporated by reference herein.

STATEMENT AS TO FEDERALLY SPONSORED RESEARCH

This invention was made with government support under Grant Nos. P01 DA028555, R01 NS036126, P01 NS031492, R01 NS034239, P01 MH064570, P01 NS043985, P30 MH062261, and R01 AG043540 awarded by the National Institutes of Health. The government has certain rights in this invention.

FIELD OF THE INVENTION

The present invention relates generally to the delivery of therapeutics. More specifically, the present invention relates to compositions and methods for the delivery of therapeutic agents to a patient for the treatment of a viral infection.

BACKGROUND OF THE INVENTION

The need to improve the bioavailability, pharmacology, cytotoxicities, and interval dosing of antiretroviral medications in the treatment of human immunodeficiency virus (HIV) infection is notable (Broder, S. (2010) Antivir. Res., 85:1-18; Este et al. (2010) Antivir. Res., 85:25-33; Moreno et al. (2010) J. Antimicrob. Chemother., 65:827-835). Since the introduction of antiretroviral therapy (ART), incidences of both mortality and co-morbidities associated with HIV-1 infection have decreased dramatically. However, many limitations associated with ART still remain which prevent full suppression of viral replication in HIV-infected individuals. These limitations include poor pharmacokinetics (PK) and biodistribution, life-long daily treatment, and multiple untoward toxic side effects (Garvie et al. (2009) J. Adolesc. Health 44:124-132; Hawkins, T. (2006) AIDS Patient Care STDs 20:6-18; Royal et al. (2009) AIDS Care 21:448-455). Since antiretroviral medications are quickly eliminated from the body and do not thoroughly penetrate all organs, dosing schedules tend to be complex and involve large amounts of drug. Patients have difficulty properly following therapy guidelines leading to suboptimal adherence and increased risk of developing viral resistance, which can result in treatment failure and accelerated progression of disease (Danel et al. (2009) J. Infect. Dis. 199:66-76). For HIV-infected patients who also experience psychiatric and mental disorders and/or drug abuse, proper adherence to therapy is even more difficult (Meade et al. (2009) AIDS Patient Care STDs 23:259-266; Baum et al. (2009) J. Acquir. Immune Defic. Syndr., 50:93-99). Accordingly, there is a need for drug delivery systems that optimize cell uptake and retention, improve intracellular stability, extend drug release, maintain antiretroviral efficacy, and minimize cellular toxicity within transporting cells.

SUMMARY OF THE INVENTION

In accordance with the instant invention, nucleoside-analog reverse transcriptase inhibitor (NRTI) prodrugs are provided. In a particular embodiment, nanoparticles comprising at least one nucleoside-analog reverse transcriptase inhibitor (NRTI) prodrug and at least one surfactant are provided. In a particular embodiment, the nucleoside-analog reverse transcriptase inhibitor prodrug has been modified to be more hydrophobic. In a particular embodiment, the sugar of the nucleoside-analog reverse transcriptase inhibitor is conjugated (e.g., at the 4'OH) with a hydrophobic aliphatic or alkyl. In a particular embodiment, the aliphatic or alkyl comprises about 3 to about 30 carbons. In a particular embodiment, R is a C4-C22 unsaturated or saturated alkyl or aliphatic. In a particular embodiment, the nucleoside-analog reverse transcriptase inhibitor (NRTI) prodrug is a 2',3'-dideoxy-3'-thiacytidine (lamivudine, 3TC) prodrug. In a particular embodiment, the nucleoside-analog reverse transcriptase inhibitor (NRTI) prodrug is an abacavir (ABC) prodrug. In a particular embodiment, the nucleoside-analog reverse transcriptase inhibitor (NRTI) prodrug is crystalline or amorphous. In a particular embodiment, the surfactant is an amphiphilic block copolymer, polysorbate, phospholipid, derivative thereof, or combination thereof. In a particular embodiment, the surfactant is an amphiphilic block copolymer. In a particular embodiment, a surfactant of the nanoparticle/nanoformulation is linked to at least one targeting ligand such as a macrophage targeting ligand (e.g., folate). An individual nanoparticle may comprise targeted and non-targeted surfactants.

Pharmaceutical compositions comprising at least one nanoparticle and/or prodrug of the instant invention and at least one pharmaceutically acceptable carrier are also provided.

According to another aspect of the instant invention, methods and uses for treating, inhibiting, or preventing a disease or disorder (e.g., a viral, particularly a retroviral (e.g., HIV) infection) in a subject are provided. In a particular embodiment, the method comprises administering to the subject at least one prodrug and/or nanoparticle/nanoformulation of the instant invention. In a particular embodiment, the method further comprises administering at least one further therapeutic agent or therapy for the disease or disorder, e.g., at least one additional anti-HIV compound.

BRIEF DESCRIPTIONS OF THE DRAWING

FIG. 1 is a graph of the cellular uptake of 3TC prodrug nanoparticles over time by human macrophages.

Figure 2:
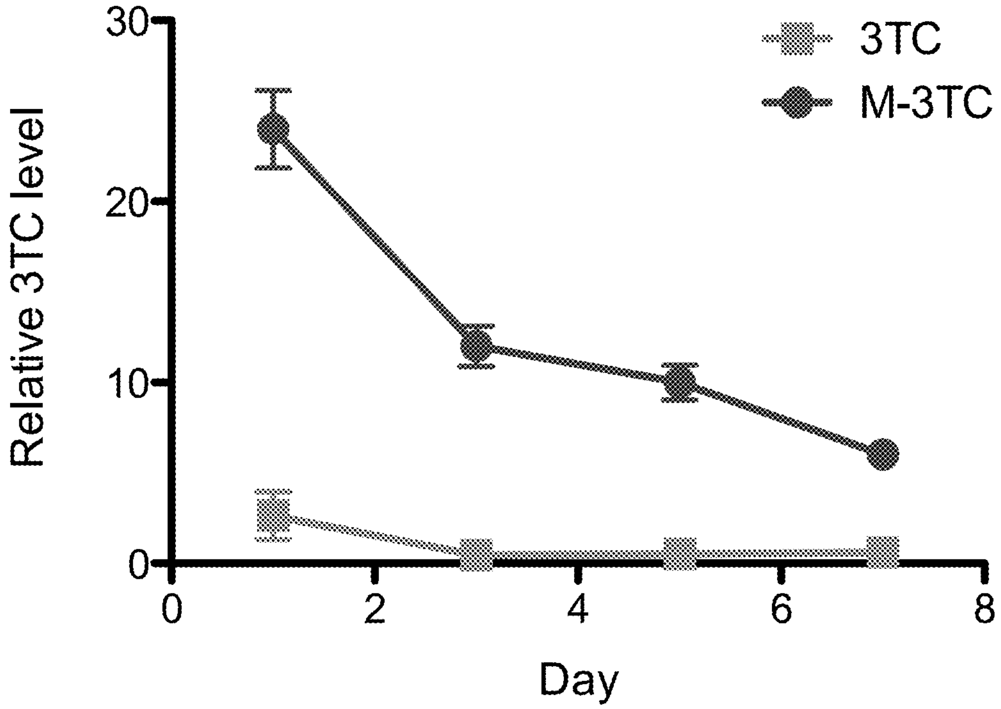

FIG. 2 provides a timecourse of 3TC plasma levels after administration of the 3TC prodrug nanoparticles to mice.

Figure 3:
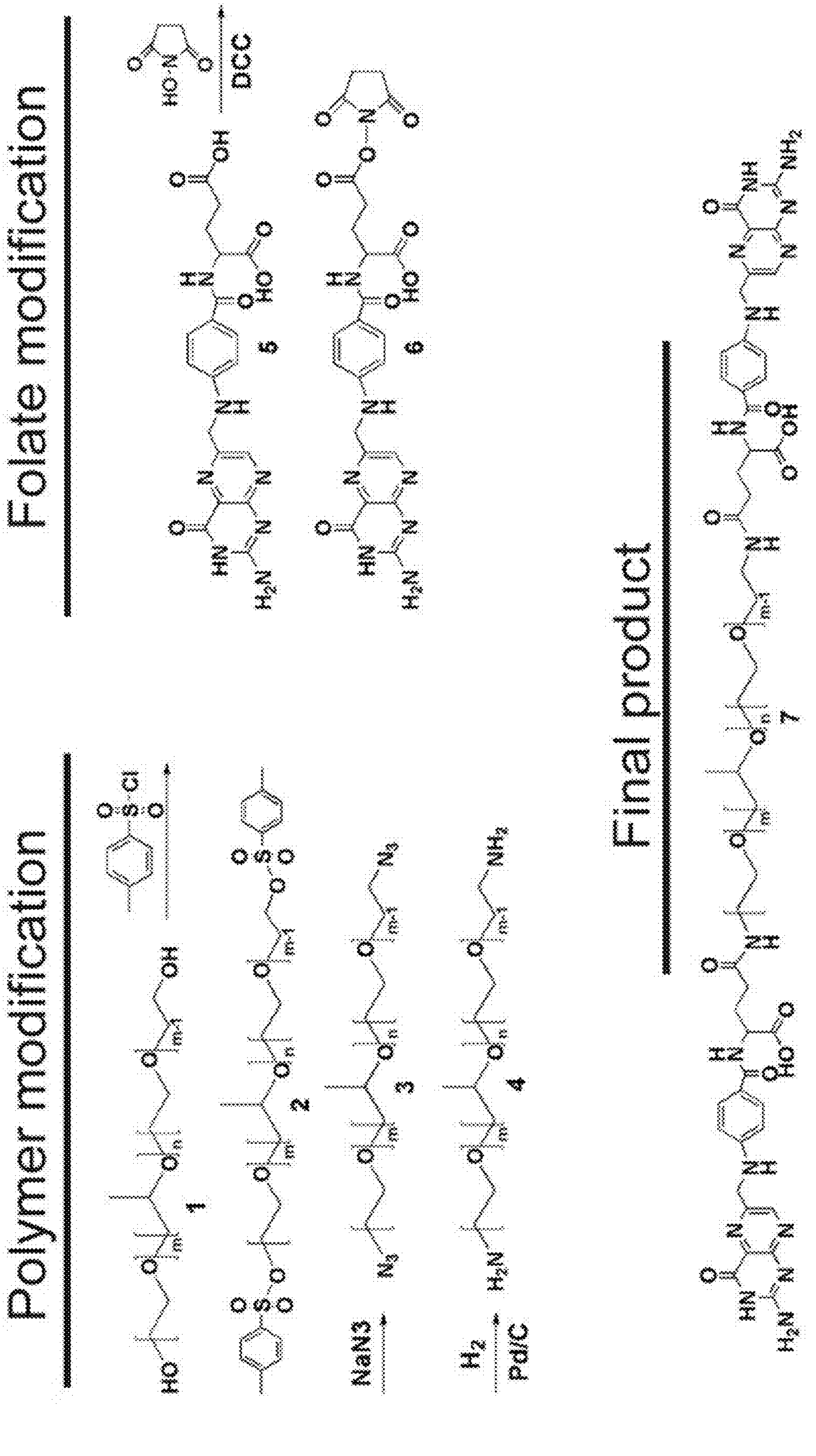

FIG. 3 provides a schematic of the addition of folate to polymer.

Figure 4:
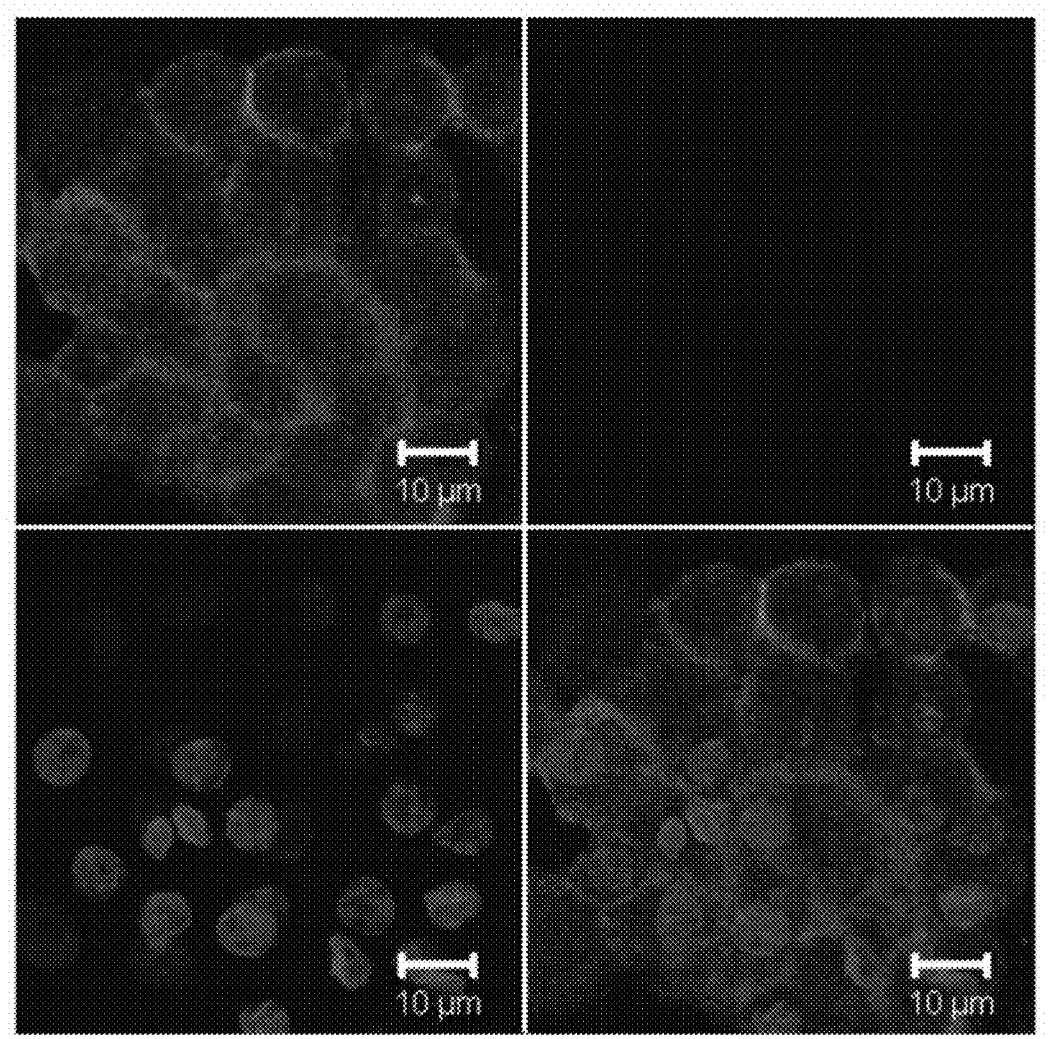

FIG. 4 shows the expression of folate receptor 2 on macrophage.

Figure 5:
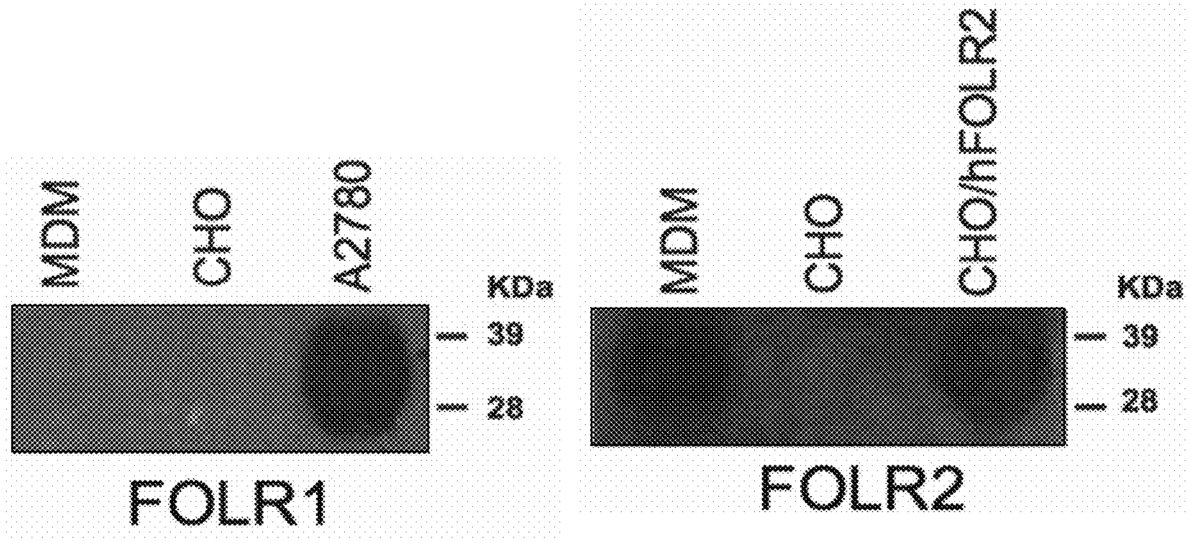

FIG. 5 provides images of Western blot analysis of the expression of folate receptor 1 (FOLR1) and 2 (FOLR2) on the indicated cell lines.

Figure 6:
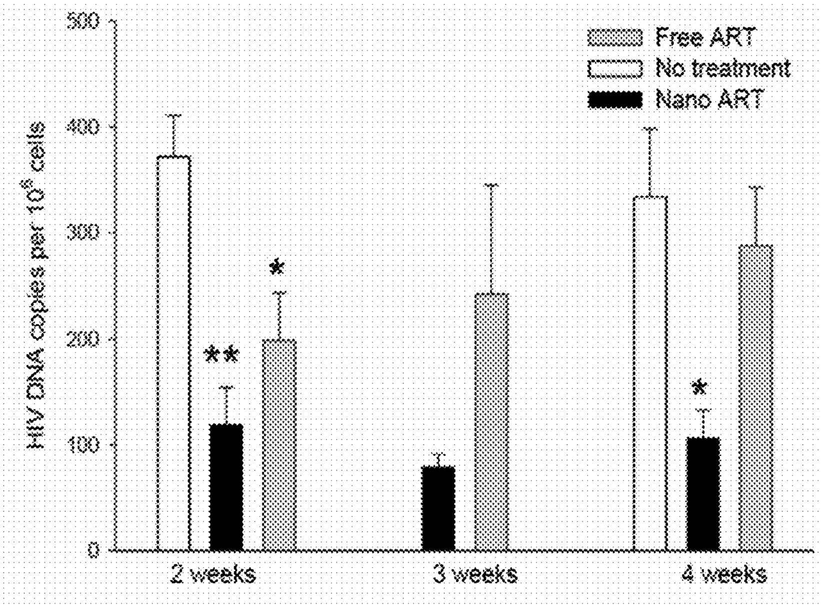
Figure 6:
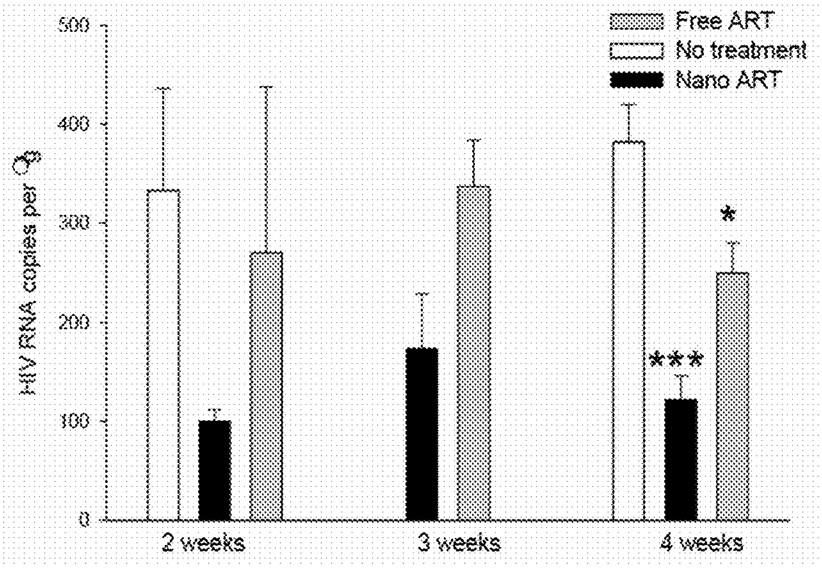
Figure 6:
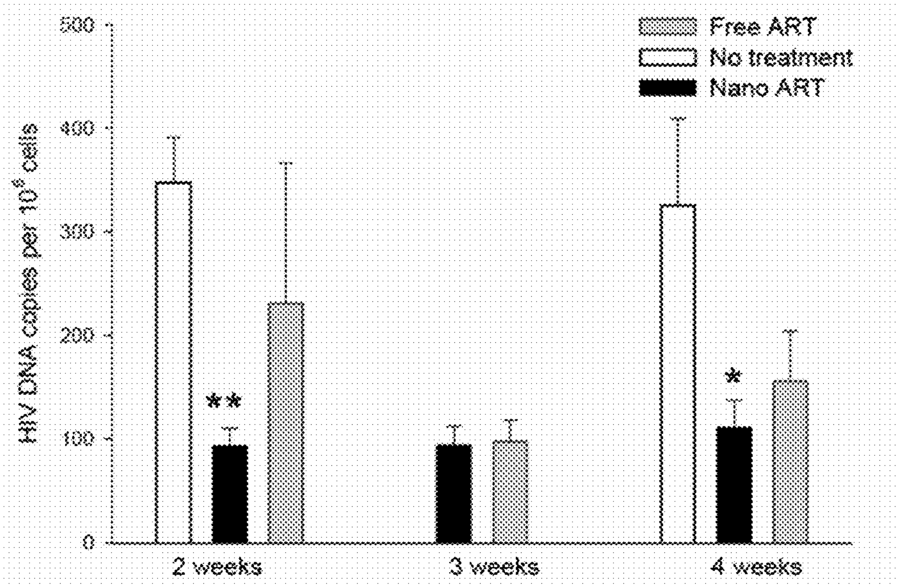

FIG. 6 provides graphs of HIV infection in the indicated tissues in mice treated with 3TC prodrug nanoparticles or free 3TC or control mice (no treatment). Three week points were not compared to no treatment. $*p<0.05$, $p<0.01$, $*p<0.005$ relative to no treatment.

DETAILED DESCRIPTION OF THE INVENTION

Treatments of viral infections, particularly HIV infections, which are currently available, include inhibitors of viral entry, nucleoside reverse transcriptase, nucleotide reverse transcriptase, integrase, and protease. Resistance is linked to a shortened drug half-life, the viral life cycle, and rapid mutations resulting in a high genetic variability. Combination therapies, e.g., antiretroviral therapies (ART), which are considered "cocktail" therapy, have gained substantial attention. Benefits include decreased viral resistance, limited toxicities, improved adherence to therapeutic regimens and sustained antiretroviral efficacy. Combination therapies minimize potential drug resistance by suppressing viral (e.g., HIV) replication, thereby reducing spontaneous resistant mutants. Treatment failure is attributed, in part, to the short drug half-life. Furthermore, failure can also be attributed, in part, to limited access to tissue and cellular viral reservoirs, thereby precluding viral eradication efforts. To these ends, the development of cell and tissue targeted nanoformulated prodrug (nanoparticle) platforms are of considerable interest in the management of viral (e.g., HIV) infections. Pre-exposure prophylaxis (PrEP) is another strategy used in the management of viral (e.g., HIV) transmission. For example, TRUVADA® (tenofovir/emtricitabine) has been approved for pre-exposure prophylaxis against HIV infection. Additionally, the combination of lamivudine and zidovudine (COMBIVIR®) has been used as pre-exposure prophylaxis and post-exposure prophylaxis.

Traditional dosage forms of antiretroviral drugs are characterized by high pill burden that lead to poor adherence. Targeted prodrug nanoparticles will improve drug biodistribution and enhance the therapeutic efficacy and the lower dosage will reduce side effects such as systemic toxicity. Further, single drug treatments may cause high genetic variability of HIV and drug resistance. In contrast, targeted combination therapeutic strategies will decrease viral resistance, improve the quality of life, and increase survival time.

The prodrugs and nanoformulated prodrugs (nanoparticles) provided herein extend the drug half-life, increase hydrophobicity, improved protein binding capacity and antiretroviral efficacy. This will benefit people who have to receive daily high doses or even several doses a day, since lower dosage with less dosing frequency would not only decrease the side effects, but also be convenient to the patients. The prodrugs and nanoformulated prodrugs (nanoparticles) provided herein may also be used as a post-exposure treatment and/or pre-exposure prophylaxis (e.g., for people who are at high risk of contracting HIV-1). In other words, the prodrugs and nanoparticles of the instant invention and their combination may be used to prevent a viral infection (e.g., HIV infection) and/or treat or inhibit an acute or long term viral infection (e.g., HIV infection). While the prodrugs and nanoparticles of the instant invention are generally described as anti-HIV agents, the prodrugs and nanoformulations of the instant invention are also effective against other viral infections including, without limitation: hepatitis B virus (HBV), hepatitis C virus (HCV), herpes simplex virus (HSV), and Ebola virus. The prodrugs and nanoformulations of the instant invention are also effective against other microbial infections such as *Mycobacterium tuberculosis.*

In accordance with the instant invention, nucleoside-analog reverse transcriptase inhibitor (NRTI) prodrugs are provided, wherein the nucleoside-analog reverse transcriptase inhibitor has been modified to be more hydrophobic. In a particular embodiment, the sugar of the nucleoside-analog reverse transcriptase inhibitor is conjugated (e.g., at the 4'OH; e.g., via an acylation reaction) with an aliphatic group or an alkyl. In a particular embodiment, the alkyl or aliphatic group is hydrophobic. In a particular embodiment, the aliphatic group or alkyl comprises about 3 to about 30 carbons, about 4 to about 28 carbons, about 12 to about 18 carbons, or about 14 carbons (e.g., in the main chain of the alkyl or aliphatic group). In a particular embodiment, R is a C4-C22 unsaturated or saturated aliphatic or alkyl chain. In a particular embodiment, R is the alkyl chain of a fatty acid (saturated or unsaturated). In a particular embodiment, the fatty acid is unsaturated. Examples of fatty acids include, without limitation: caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. In a particular embodiment, the fatty acid is myristic acid.

In a particular embodiment, 2',3'-dideoxy-3'-thiacytidine (lamivudine, 3TC) and abacavir (ABC) prodrugs are provided. In a particular embodiment, the 3TC prodrug has the following formula:

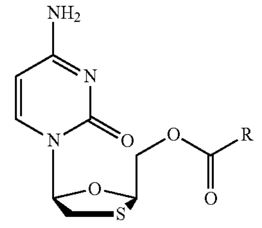

wherein R is an aliphatic group or an alkyl. In a particular embodiment, the alkyl or aliphatic group is hydrophobic. In a particular embodiment, the aliphatic group or alkyl comprises about 3 to about 30 carbons, about 4 to about 28 carbons, about 12 to about 18 carbons, or about 14 carbons (e.g., in the main chain of the alkyl or aliphatic group). In a particular embodiment, R is a C4-C22 unsaturated or saturated aliphatic or alkyl chain. In a particular embodiment, R is the alkyl chain of a fatty acid (saturated or unsaturated). In a particular embodiment, the fatty acid is unsaturated. Examples of fatty acids include, without limitation: caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. In a particular embodiment, the fatty acid is myristic acid.

In a particular embodiment, the abacavir prodrug has the following formula:

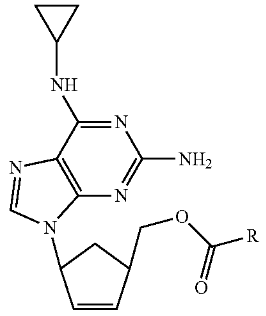

wherein R is an aliphatic group or an alkyl. In a particular embodiment, the alkyl or aliphatic group is hydrophobic. In a particular embodiment, the aliphatic or alkyl comprises about 3 to about 30 carbons, about 4 to about 28 carbons, about 12 to about 18 carbons, or about 14 carbons (e.g., in the main chain of the alkyl or aliphatic). In a particular embodiment, R is a C4-C22 unsaturated or saturated alkyl or aliphatic chain. In a particular embodiment, R is the alkyl chain of a fatty acid (saturated or unsaturated). In a particular embodiment, the fatty acid is unsaturated. Examples of fatty acids include, without limitation: caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. In a particular embodiment, the fatty acid is myristic acid.

Methods of synthesizing hydrophobic NRTI prodrugs are encompassed by the instant invention. In a particular embodiment, the NRTI prodrugs are synthesized through the conjugation of a hydrophobic group such as an aliphatic or alkyl group (e.g., a fatty acid) to the NRTI. In a particular embodiment, the hydrophobic group is conjugated to the NRTI via the —OH (e.g., the 4'-OH group) of the sugar (e.g., ribose/deoxyribose) (e.g., via an acylation reaction). In a particular embodiment, the hydrophobic group is conjugated through direct conjugation with a fatty acid under acidic conditions or through a group protection and deprotection method. Provided below is a scheme illustrating a method for synthesizing an NRTI prodrug (a 3TC prodrug is exemplified, but similar methods can be employed for other NRTI) of the instant invention. The reagents, solvents and reaction conditions are illustrative.

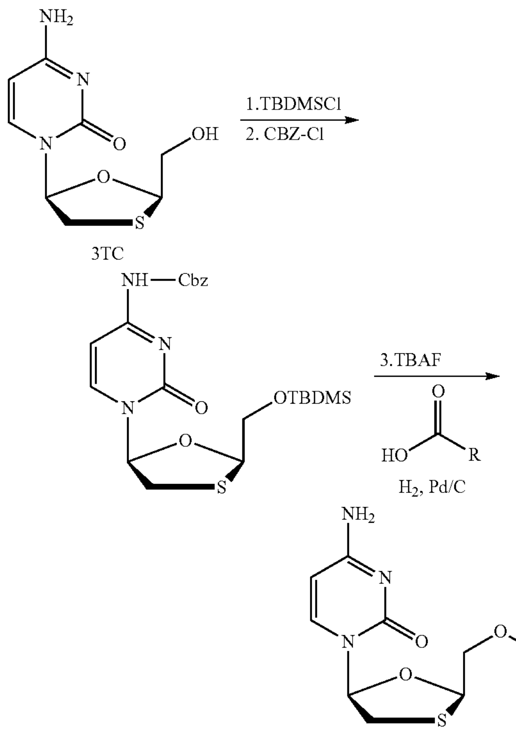

3TC

3TC derivative

In a particular embodiment, NRTI prodrugs can be prepared according to the following steps: 1) orthogonal protection of amine and hydroxyl functional groups to control chemoselectivity of the reaction; 2) liberation of the hydroxyl group and subsequent reaction with the alkyl or aliphatic group (e.g., alkyl fatty acid (e.g., acyl chloride or activated carboxylic acid of the alkyl fatty acid)); and 3) deprotection of the amine to generate the desired compound.

For step 1, hydroxyl-protecting groups include, without limitation, esters, acetyls, and ethers such as base sensitive groups like t-butyldimethylsilyl chloride (TBDMS-Cl) and t-butyldiphenylsilyl chloride. Other hydroxyl-protecting groups include, without limitation, phenylmethyl ether, trimethylsilyl ether, methoxymethyl ether, tetrahydropyranyl ether, t-butyl ether, allyl ether, benzyl ether, acetic acid ester, pivalic acid ester, and benzoic acid ester. The base used in this step may include amines such as, without limitation: pyridine, triethylamine, 4-dimethylaminopyridine, etc. Polar aprotic solvents such as N, N-dimethyl formamide and tetrahydrofuran may be used to run the reaction. The reagents can be mixed at 0° C. and gradually warmed to temperature over time (e.g., 4-24 hours). The hydroxyl-protected compounds can be purified by conventional methods such as column chromatography.

In step 2, amine groups may be protected, for example, with acid, base, or a hydrogenolysis labile group. Examples of amine protecting groups include, without limitation: chloroformates (e.g., benzyl chloroformate to yield a carboxybenzyl (Cbz) protected amine), trityl chloride, chloro-4,4'-dimethoxytriphenylmethane, carbobenzyloxy, p-methoxybenzyl carbonyl, tert-butyloxycarbonyl (BOC), 9-fluorenylmethyloxycarbonyl (FMOC), acetyl, benzoyl, benzyl, carbamate, p-methoxybenzyl, 3,4-dimethoxybenzyl, p-methoxyphenyl, tosyl, and sulfonamides. The base used in this step may include amines such as, without limitation: pyridine, triethylamine, 4-dimethylaminopyridine, etc. Pyridine, N, N-dimethyl formamide or THF may be used as solvents. The protected compounds may be purified by conventional methods such as column chromatography.

In step 3, the hydroxyl group may be deprotected using the appropriate reagent. The alcohol may then be coupled with an aliphatic or alkyl group (e.g., a hydrophobic aliphatic or alkyl group; e.g., a fatty acyl chloride or activated carboxylic acid) to furnish the amine-protected prodrugs. The coupling reagents used to activate the carboxylic acid include, without limitation: uranium salts, carbodiimide reagents, phosphonium salts, etc. The base may include, without limitation: triethylamine, N, N-diisopropylethylamine, collidine, etc. Polar aprotic solvents such as N, N-dimethyl formamide and acetonitrile may be used in the coupling reaction. The reagents may be mixed at 0° C. and gradually warmed to temperature (e.g., over 12-24 hours). The N-protected compounds may then be purified by conventional methods such as column chromatography. The amine-protecting group may then be cleaved with the appropriate reagents to deliver the desired prodrug. The final compounds may also then be purified by conventional methods such as column chromatography.

The instant invention also encompasses nanoparticles (sometimes referred to herein as nanoformulations) for the delivery of compounds to a cell. In a particular embodiment, the nanoparticle is for the delivery of antiretroviral therapy to a subject. The nanoparticles of the instant invention comprise at least one antiretroviral and at least one surfactant. In a particular embodiment, the nanoparticles comprise a spectroscopic-defined polymer: drug ratio that maintains optimal targeting of the drug nanoparticle to maintain a macrophage depot. These components of the nanoparticle, along with other optional components, are described hereinbelow.

Methods of synthesizing the nanoparticles of the instant invention are known in the art. In a particular embodiment, the methods generate nanoparticles comprising a therapeutic (e.g., crystalline or amorphous) coated (either partially or completely) with a surfactant. Examples of synthesis methods include, without limitation, milling (e.g., wet milling), homogenization (e.g., high pressure homogenization), particle replication in nonwetting template (PRINT) technology, and/or sonication techniques. For example, U.S. Patent Application Publication No. 2013/0236553, incorporated by reference herein, provides methods suitable for synthesizing nanoparticles of the instant invention. In a particular embodiment, the surfactants are firstly chemically modified with targeting ligands and then used directly or mixed with non-targeted surfactants in certain molar ratios to coat on the surface of drug suspensions—e.g., by using a nanoparticle synthesis process (e.g., a crystalline nanoparticle synthesis process) such as milling (e.g., wet milling), homogenization (e.g., high pressure homogenization), particle replication in nonwetting template (PRINT) technology, and/or sonication techniques, thereby preparing targeted nanoformulations. The nanoparticles may be used with or without further purification, although the avoidance of further purification is desirable for quicker production of the nanoparticles. In a particular embodiment, the nanoparticles are synthesized using milling and/or homogenization. Targeted nanoparticles (e.g., using ligands with high molecular weight) may be developed through either physically or chemically coating and/or binding on the surface of surfactants and/or drug nanosuspensions.

The nanoparticles of the instant invention may be used to deliver any agent(s) or compound(s), particularly bioactive agents, particularly therapeutic agents (e.g., antiviral compounds) or diagnostic agents to a cell or a subject (including non-human animals). The nanoparticles of the instant invention may be used to deliver at least one prodrug of the instant invention to a cell or a subject (including non-human animals). The nanoparticles of the instant invention may comprise at least one therapeutic agent, particularly at least one antiviral or antiretroviral. In a particular embodiment, the nanoparticles of the instant invention comprise at least two therapeutic agents, particularly wherein at least one is a prodrug of the instant invention. For example, the nanoparticle may comprise a nucleoside-analog reverse transcriptase inhibitor (NRTI) prodrug of the instant invention and at least one other therapeutic agent (e.g., an anti-HIV agent). The nanoparticle may comprise a 3TC prodrug of the instant invention and at least one other therapeutic agent (e.g., an anti-HIV agent). The nanoparticle may comprise an abacavir prodrug of the instant invention and at least one other therapeutic agent (e.g., an anti-HIV agent). The nanoparticle may comprise an abacavir prodrug of the instant invention, a 3TC produg of the instant invention, and, optionally, at least one other therapeutic agent (e.g., an anti-HIV agent).

In a particular embodiment, the nanoparticles are a submicron colloidal dispersion of nanosized drug crystals stabilized by surfactants (e.g., surfactant-coated drug crystals; a nanoformulation). In a particular embodiment, the nanoparticles (or the therapeutic agent of the nanoparticles) may be crystalline (solids having the characteristics of crystals), amorphous, or are solid-state nanoparticles of the therapeutic agent that is formed as crystal that combines the drug and surfactant. As used herein, the term "crystalline" refers to an ordered state (i.e., non-amorphous) and/or a substance exhibiting long-range order in three dimensions. In a particular embodiment, the majority (e.g., at least 50%, 60%, 70%, 80%, 90%, 95% or more) of the therapeutic agent (and, optionally the hydrophobic portion of the surfactant) are crystalline.

In a particular embodiment, the nanoparticles are synthesized by adding the therapeutic agent (e.g., optionally in free base form) to a surfactant (described below) solution and then generating the nanoparticles (e.g., by wet milling or high pressure homogenization). The therapeutic agent and surfactant solution may be agitated prior the wet milling or high pressure homogenization.

In a particular embodiment, the resultant nanoparticle is up to about 2 or 3 μm in diameter (e.g., z-average diameter) or its longest dimension, particularly up to about 1 μm (e.g., about 100 nm to about 1 μm). For example, the diameter or longest dimension of the nanoparticle may be about 50 to about 800 nm. In a particular embodiment, the diameter or longest dimension of the nanoparticle is about 50 to about 750 nm, about 50 to about 500 nm, about 200 nm to about 500 nm, about 250 nm to about 350 nm, or about 300 nm to about 350 nm. The nanoparticles may be, for example, rod shaped, elongated rods, irregular, or round shaped. The nanoparticles of the instant invention may be neutral or charged. The nanoparticles may be charged positively or negatively.

The therapeutic agent may be hydrophobic, a water insoluble compound, or a poorly water soluble compound. For example, the therapeutic agent may have a solubility of less than about 10 mg/ml, less than 1 mg/ml, more particularly less than about 100 μg/ml, and more particularly less than about 25 μg/ml in water or aqueous media in a pH range of 0-14, preferably between pH 4 and 10, particularly at 20° C.

In a particular embodiment, the therapeutic agent is an antiviral, more particularly an antiretroviral. The antiretroviral may be effective against or specific to lentiviruses. Lentiviruses include, without limitation, human immunodeficiency virus (HIV) (e.g., HIV-1, HIV-2), bovine immunodeficiency virus (BIV), feline immunodeficiency virus (FIV), simian immunodeficiency virus (SIV), and equine infectious anemia virus (EIA).

In a particular embodiment, the therapeutic agent is a nucleoside-analog reverse transcriptase inhibitor (NRTI) prodrug comprising a hydrophobic moiety conjugated to the sugar, particularly a hydrophobic aliphatic or alkyl group. In a particular embodiment, the therapeutic agent is a 3TC prodrug as described herein. In a particular embodiment, the therapeutic agent is an abacavir prodrug as described herein. As explained hereinabove, the nanoparticles may comprise at least a second therapeutic agent, particularly an anti-HIV agent.

An anti-HIV compound or an anti-HIV agent is a compound which inhibits HIV. Examples of an anti-HIV agent include, without limitation:

(I) Nucleoside-analog reverse transcriptase inhibitors (NRTIs). NRTIs refer to nucleosides and nucleotides and analogues thereof that inhibit the activity of reverse transcriptase, particularly HIV-1 reverse transcriptase. NRTIs comprise a sugar and base. Examples of nucleoside-analog reverse transcriptase inhibitors include, without limitation, adefovir dipivoxil, adefovir, lamivudine, telbivudine, entecavir, tenofovir, stavudine, abacavir, didanosine, emtricitabine, zalcitabine, and zidovudine.

(II) Non-nucleoside reverse transcriptase inhibitors (NNRTIs). NNRTIs are allosteric inhibitors which bind reversibly at a nonsubstrate-binding site on reverse transcriptase, particularly the HIV reverse transcriptase, thereby altering the shape of the active site or blocking polymerase activity. Examples of NNRTIs include, without limitation, delavirdine (BHAP, U-90152; RESCRIPTOR®), efavirenz (DMP-266, SUSTIVA®), nevirapine (VIRAMUNE®), PNU-142721, capravirine (S-1153, AG-1549), emivirine (+)-calanolide A (NSC-675451) and B, etravirine (TMC-125), rilpivirne (TMC278, Edurant™), DAPY (TMC120), BILR-355 BS, PHI-236, and PHI-443 (TMC-278).

(III) Protease inhibitors (PI). Protease inhibitors are inhibitors of a viral protease, particularly the HIV-1 protease. Examples of protease inhibitors include, without limitation, darunavir, amprenavir (141W94, AGENERASE®), tipranivir (PNU-140690, APTIVUS®), indinavir (MK-639; CRIXIVAN®), saquinavir (INVIRASE®, FORTOVASE®), fosamprenavir (LEXIVAR), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515.

(IV) Fusion or entry inhibitors. Fusion or entry inhibitors are compounds, such as peptides, which block HIV entry into a cell (e.g., by binding to HIV envelope protein and blocking the structural changes necessary for the virus to fuse with the host cell). Examples of fusion inhibitors include, without limitation, CCR5 receptor antagonists (e.g., maraviroc (Selzentry®, Celsentri)), enfuvirtide (INN, FUZEON®), T-20 (DP-178, FUZEON®) and T-1249.

(V) Integrase inhibitors. Integrase inhibitors are a class of antiretroviral drug designed to block the action of integrase (e.g., HIV integrase), a viral enzyme that inserts the viral genome into the DNA of the host cell. Examples of integrase inhibitors include, without limitation, raltegravir, elvitegravir, GSK1265744 (cabotegravir), GSK1349572 (dolutegravir), and MK-2048.

Anti-HIV compounds also include maturation inhibitors (e.g., bevirimat). Maturation inhibitors are typically compounds which bind HIV gag and disrupt its processing during the maturation of the virus. Anti-HIV compounds also include HIV vaccines such as, without limitation, ALVAC® HIV (vCP1521), AIDSVAX® B/E (gp120), and combinations thereof. Anti-HIV compounds also include HIV antibodies (e.g., antibodies against gp120 or gp41), particularly broadly neutralizing antibodies.

More than one anti-HIV agent may be used, particularly where the agents have different mechanisms of action (as outlined above). For example, anti-HIV agents which are not NRTIs may be combined with the NRTI prodrugs of the instant invention. In a particular embodiment, the anti-HIV therapy is highly active antiretroviral therapy (HAART).

As stated hereinabove, the nanoparticles of the instant invention comprise at least one surfactant. A "surfactant" refers to a surface-active agent, including substances commonly referred to as wetting agents, detergents, dispersing agents, or emulsifying agents. Surfactants are usually organic compounds that are amphiphilic.

Examples of surfactants include, without limitation, synthetic or natural phospholipids, PEGylated lipids (e.g., PEGylated phospholipid), lipid derivatives, polysorbates, amphiphilic copolymers, amphiphilic block copolyemers, poly(ethylene glycol)-co-poly(lactide-co-glycolide) (PEG-PLGA), their derivatives, ligand-conjugated derivatives and combinations thereof. Other surfactants and their combinations that can form stable nanosuspensions and/or can chemically/physically bind to the targeting ligands of HIV infectable/infected CD4+ T cells, macrophages and dendritic cells can be used in the instant invention. Further examples of surfactants include, without limitation: 1) nonionic surfactants (e.g., pegylated and/or polysaccharide-conjugated polyesters and other hydrophobic polymeric blocks such as poly(lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene); glyceryl esters, polyoxyethylene fatty alcohol ethers, polyoxyethylene sorbitan fatty acid esters, polyoxyethylene fatty acid esters, sorbitan esters, glycerol monostearate, polyethylene glycols, polypropyleneglycols, cetyl alcohol, cetostearyl alcohol, stearyl alcohol, aryl alkyl polyether alcohols, polyoxyethylene-polyoxypropylene copolymers, poloxamines, cellulose, methylcellulose, hydroxylmethylcellulose, hydroxypropylcellulose, hydroxypropylmethylcellulose, polysaccharides, starch and their derivatives, hydroxyethylstarch, polyvinyl alcohol (PVA), polyvinylpyrrolidone, and their combination thereof); and 2) ionic surfactants (e.g., phospholipids, amphiphilic lipids, 1,2-dialkylglycero-3-alkylphophocholines, 1,2-distearoyl-sn-glecro-3-phosphocholine (DSPC), 1,2-distearoyl-sn-glycero-3-phosphoethanolamine-N-[carboxy(polyethylene glycol) (DSPE-PEG), dimethylaminoethanecarbamoyl cheolesterol (DC-Chol), N-[1-(2,3-Dioleoyloxy) propyl]-N,N,N-trimethylammonium (DOTAP), alkyl pyridinium halides, quaternary ammonium compounds, lauryldimethylbenzylammonium, acyl carnitine hydrochlorides, dimethyldioctadecylammonium (DDAB), n-octylamines, oleylamines, benzalkonium, cetyltrimethylammonium, chitosan, chitosan salts, poly(ethylenimine) (PEI), poly(N-isopropyl acrylamide (PNIPAM), and poly(allylamine) (PAH), poly(dimethyldiallylammonium chloride) (PDDA), alkyl sulfonates, alkyl phosphates, alkyl phosphonates, potassium laurate, triethanolamine stearate, sodium lauryl sulfate, sodium dodecylsulfate, alkyl polyoxyethylene sulfates, alginic acid, alginic acid salts, hyaluronic acid, hyaluronic acid salts, gelatins, dioctyl sodium sulfosuccinate, sodium carboxymethylcellulose, cellulose sulfate, dextran sulfate and carboxymethylcellulose, chondroitin sulfate, heparin, synthetic poly(acrylic acid) (PAA), poly(methacrylic acid) (PMA), poly(vinyl sulfate) (PVS), poly(styrene sulfonate) (PSS), bile acids and their salts, cholic acid, deoxycholic acid, glycocholic acid, taurocholic acid, glycodeoxycholic acid, derivatives thereof, and combinations thereof).

In a particular embodiment of the invention, the surfactant is present in the nanoparticle and/or surfactant solution to synthesize the nanoparticle (as described hereinabove) at a concentration ranging from about 0.0001% to about 10% or 15% by weight. In a particular embodiment, the concentration of the surfactant ranges from about 0.01% to about 5%, about 0.01% to about 3%, or about 0.1% to about 2% by weight. In a particular embodiment, the nanoparticle comprises at least about 50%, 75%, 80%, 85%, 90%, 95%, 97%, 98%, 99% or higher therapeutic agent by weight.

The surfactant of the instant invention may be charged or neutral. In a particular embodiment, the surfactant is neutral or negatively charged (e.g., poloxamers, polysorbates, phospholipids, and their derivatives).

In a particular embodiment, the surfactant is an amphiphilic block copolymer or lipid derivative. In a particular, embodiment, at least one surfactant of the nanoparticle is an amphiphilic block copolymer, particularly a copolymer comprising at least one block of poly(oxyethylene) and at least one block of poly(oxypropylene). In a particular embodiment, the surfactant is a triblock amphiphilic block copolymer. In a particular embodiment, the surfactant is poloxamer 407.

In a particular embodiment, the amphiphilic block copolymer is a copolymer comprising at least one block of poly(oxyethylene) and at least one block of poly(oxypropylene). Amphiphilic block copolymers are exemplified, without limitation, by the block copolymers having the formulas:

(I)

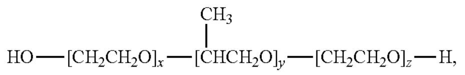

(II)

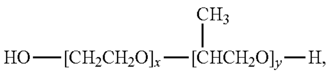

(III)

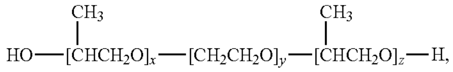

(IV)

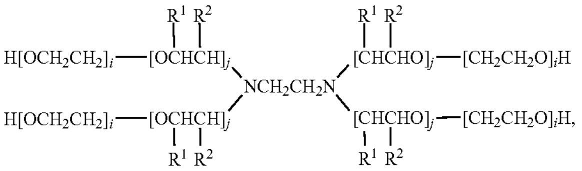

(V)

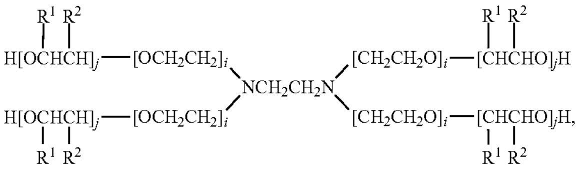

in which x, y, z, i, and j have values from about 2 to about 800, particularly from about 5 to about 200 or about 5 to about 80, and wherein for each $R^1$, $R^2$ pair, as shown in formula (IV) and (V), one is hydrogen and the other is a methyl group. The ordinarily skilled artisan will recognize that the values of x, y, and z will usually represent a statistical average and that the values of x and z are often, though not necessarily, the same. Formulas (I) through (III) are oversimplified in that, in practice, the orientation of the isopropylene radicals within the B block will be random. This random orientation is indicated in formulas (IV) and (V), which are more complete. Such poly(oxyethylene)-poly(oxypropylene) compounds have been described by Santon (Am. Perfumer Cosmet. (1958) 72(4):54-58); Schmolka (Loc. cit. (1967) 82(7):25-30), Schick, ed. (Non-ionic Suifactants, Dekker, N.Y., 1967 pp. 300-371). A number of such compounds are commercially available under such generic trade names as "lipoloxamers", "Pluronics®," "poloxamers," and "synperonics." Pluronic® copolymers within the B-A-B formula, as opposed to the A-B-A formula typical of Pluronics®, are often referred to as "reversed" Pluronics®, "Pluronic® R" or "meroxapol." Generally, block copolymers can be described in terms of having hydrophilic "A" and hydrophobic "B" block segments. Thus, for example, a copolymer of the formula A-B-A is a triblock copolymer consisting of a hydrophilic block connected to a hydrophobic block connected to another hydrophilic block. The "polyoxamine" polymer of formula (IV) is available from BASF under the tradename Tetronic®. The order of the polyoxyethylene and polyoxypropylene blocks represented in formula (IV) can be reversed, creating Tetronic R®, also available from BASF (see, Schmolka, J. Am. Oil. Soc. (1979) 59:110).

Polyoxypropylene-polyoxyethylene block copolymers can also be designed with hydrophilic blocks comprising a random mix of ethylene oxide and propylene oxide repeating units. To maintain the hydrophilic character of the block, ethylene oxide can predominate. Similarly, the hydrophobic block can be a mixture of ethylene oxide and propylene oxide repeating units. Such block copolymers are available from BASF under the tradename Pluradot™. Poly(oxyethylene)-poly(oxypropylene) block units making up the first segment need not consist solely of ethylene oxide. Nor is it necessary that all of the B-type segment consist solely of propylene oxide units. Instead, in the simplest cases, for example, at least one of the monomers in segment A may be substituted with a side chain group.

A number of poloxamer copolymers are designed to meet the following formula:

(I)

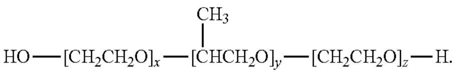

Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. Pluronic® block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the weight content of EO block in tens of weight percent (for example, 80% weight if the digit is 8, or 10% weight if the digit is 1). The remaining first one or two digits encode the molecular mass of the central PO block. To decipher the code, one should multiply the corresponding number by 300 to obtain the approximate molecular mass in daltons (Da). Therefore Pluronic® nomenclature provides a convenient approach to estimate the characteristics of the block copolymer in the absence of reference literature. For example, the code 'F127' defines the block copolymer, which is a solid, has a PO block of 3600 Da (12×300) and 70% weight of EO. The precise molecular characteristics of each Pluronic® block copolymer can be obtained from the manufacturer.

Other biocompatible amphiphilic copolymers include those described in Gaucher et al. (J. Control Rel. (2005) 109:169-188. Examples of other polymers include, without limitation, poly(2-oxazoline) amphiphilic block copolymers, polyethylene glycol-polylactic acid (PEG-PLA), PEG-PLA-PEG, polyethylene glycol-poly(lactide-co-glycolide) (PEG-PLG), polyethylene glycol-poly(lactic-co-glycolic acid) (PEG-PLGA), polyethylene glycol-polycaprolactone (PEG-PCL), polyethylene glycol-polyaspartate (PEG-PAsp), polyethylene glycol-poly(glutamic acid) (PEG-PGlu), polyethylene glycol-poly(acrylic acid) (PEG-PAA), polyethylene glycol-poly(methacrylic acid) (PEG-PMA), polyethylene glycol-poly(ethyleneimine) (PEG-PEI), polyethylene glycol-poly(L-lysine) (PEG-PLys), polyethylene glycol-poly(2-(N,N-dimethylamino)ethyl methacrylate) (PEG-PDMAEMA), polyethylene glycol-chitosan, and derivatives thereof.

In a particular embodiment, the surfactant is poloxamer 407 (Pluronic® F127).

The surfactant of the instant invention may be linked to a targeting ligand. A targeting ligand is a compound that specifically binds to a specific type of tissue or cell type (e.g., in a desired target: cell ratio). For example, a targeting ligand may be used for engagement or binding of a target cell (e.g., a macrophage) surface marker or receptor which may facilitate its uptake into the cell (e.g., within a protected subcellular organelle that is free from metabolic degradation). In a particular embodiment, the targeting ligand is a ligand for a cell surface marker/receptor. The targeting ligand may be an antibody or fragment thereof immunologically specific for a cell surface marker (e.g., protein or carbohydrate) preferentially or exclusively expressed on the targeted tissue or cell type. The targeting ligand may be linked directly to the surfactant or via a linker. Generally, the linker is a chemical moiety comprising a covalent bond or a chain of atoms that covalently attaches the ligand to the surfactant. The linker can be linked to any synthetically feasible position of the ligand and the surfactant. Exemplary linkers may comprise at least one optionally substituted; saturated or unsaturated; linear, branched or cyclic aliphatic group, an alkyl group, or an optionally substituted aryl group. The linker may be a lower alkyl or aliphatic. The linker may also be a polypeptide (e.g., from about 1 to about 10 amino acids, particularly about 1 to about 5). In a particular embodiment, the targeting moiety is linked to either of both ends of the surfactant. The linker may be non-degradable and may be a covalent bond or any other chemical structure which cannot be substantially cleaved or cleaved at all under physiological environments or conditions.

The nanoparticles/nanoformulations of the instant invention may comprise targeted and/or non-targeted surfactants. In a particular embodiment, the molar ratio of targeted and non-targeted surfactants in the nanoparticles/nanoformulations of the instant invention is from about 0.001 to 100%, about 1% to about 99%, about 5% to about 95%, about 10% to about 90%, about 25% to about 75%, about 30% to about 60%, or about 40%. In a particular embodiment, the nanoparticle comprises only targeted surfactants. In a particular embodiment, the nanoparticles/nanoformulations of the instant invention comprise a folate targeted surfactant and a non-targeted version of the surfactant. In a particular embodiment, the nanoparticles/nanoformulations of the instant invention comprise folate-poloxamer 407 (FA-P407) and/or poloxamer 407.

The targeted nanoformulations of the instant invention may comprise a targeting ligand for directing the nanoparticles to HIV tissue and cellular sanctuaries/reservoirs (e.g., central nervous system, gut associated lymphoid tissues (GALT), CD4+ T cells, macrophages, dendritic cells, etc.). In a particular embodiment, the targeting ligand is a macrophage targeting ligand; CD4+ T cell targeting ligand, or a dendritic cell targeting ligand. Macrophage targeting ligands include, without limitation, folate receptor ligands (e.g., folate (folic acid) and folate receptor antibodies and fragments thereof (see, e.g., Sudimack et al. (2000) Adv. Drug Del. Rev., 41:147-162)), mannose receptor ligands (e.g., mannose), formyl peptide receptor (FPR) ligands (e.g., N-formyl-Met-Leu-Phe (fMLF)), and tuftsin (the tetrapeptide Thr-Lys-Pro-Arg). Other targeting ligands (e.g., for targeting HIV reservoirs) include, without limitation, hyaluronic acid, gp120 and peptide fragments thereof, and ligands or antibodies specific for CD4, CCR5, CXCR4, CD7, CD111, CD204, CD49a, or CD29. As demonstrated hereinbelow, the targeting of the nanoparticles (e.g., to macrophage) provides for superior targeting, decreased excretion rates, decreased toxicity, and prolonged half life compared to free drug or non-targeted nanoparticles.

The instant invention encompasses pharmaceutical compositions comprising at least one nanoparticle of the instant invention (sometimes referred to herein as nanoART) and at least one pharmaceutically acceptable carrier. As stated hereinabove, the nanoparticle may comprise more than one therapeutic agent. In a particular embodiment, the pharmaceutical composition comprises a first nanoparticle comprising a first therapeutic agent(s) and a second nanoparticle comprising a second therapeutic agent(s), wherein the first and second therapeutic agents are different. The pharmaceutical compositions of the instant invention may further comprise other therapeutic agents (e.g., other anti-HIV compounds (e.g., those described herein)).

The present invention also encompasses methods for preventing, inhibiting, and/or treating a viral infection, particularly retroviral or lentiviral infections, particularly HIV infections (e.g., HIV-1). The pharmaceutical compositions of the instant invention can be administered to an animal, in particular a mammal, more particularly a human, in order to treat/inhibit an HIV infection. The pharmaceutical compositions of the instant invention may also comprise at least one other antiviral agent, particularly at least one other anti-HIV compound/agent. The additional anti-HIV compound may also be administered in a separate pharmaceutical composition from the anti-HIV NPs of the instant invention. The pharmaceutical compositions may be administered at the same time or at different times (e.g., sequentially).

The dosage ranges for the administration of the pharmaceutical compositions of the invention are those large enough to produce the desired effect (e.g., curing, relieving, treating, and/or preventing the HIV infection, the symptoms of it (e.g., AIDS, ARC), or the predisposition towards it). In a particular embodiment, the pharmaceutical composition of the instant invention is administered to the subject at an amount from about 5 μg/kg to about 500 mg/kg. In a particular embodiment, the pharmaceutical composition of the instant invention is administered to the subject at an amount greater than about 5 μg/kg, greater than about 50 μg/kg, greater than about 0.1 mg/kg, greater than about 0.5 mg/kg, greater than about 1 mg/kg, or greater than about 5 mg/kg. In a particular embodiment, the pharmaceutical composition of the instant invention is administered to the subject at an amount from about 0.5 mg/kg to about 100 mg/kg, about 10 mg/kg to about 100 mg/kg, or about 15 mg/kg to about 50 mg/kg. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The nanoparticles described herein will generally be administered to a patient as a pharmaceutical composition. The term "patient" as used herein refers to human or animal subjects. These nanoparticles may be employed therapeutically, under the guidance of a physician.

The pharmaceutical compositions comprising the nanoparticles of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the nanoparticles in the chosen medium may be varied and the medium may be chosen based on the desired route of administration of the pharmaceutical composition. Except insofar as any conventional media or agent is incompatible with the nanoparticles to be administered, its use in the pharmaceutical composition is contemplated.

The dose and dosage regimen of nanoparticles according to the invention that are suitable for administration to a particular patient may be determined by a physician considering the patient's age, sex, weight, general medical condition, and the specific condition for which the nanoparticles are being administered and the severity thereof. The physician may also take into account the route of administration, the pharmaceutical carrier, and the nanoparticle's biological activity.

Selection of a suitable pharmaceutical composition will also depend upon the mode of administration chosen. For example, the nanoparticles of the invention may be administered by direct injection or intravenously. In this instance, a pharmaceutical composition comprises the nanoparticle dispersed in a medium that is compatible with the site of injection.

Nanoparticles of the instant invention may be administered by any method. For example, the nanoparticles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the nanoparticles are administered intramuscularly, subcutaneously, or to the bloodstream (e.g., intravenously). Pharmaceutical compositions for injection are known in the art. If injection is selected as a method for administering the nanoparticle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a nanoparticle of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. In a particular embodiment, the nanoformulations of the instant invention, due to their long-acting therapeutic effect, may be administered once every 1 to 12 months or even less frequently. For example, the nanoformulations of the instant invention may be administered once every 0.5, 1, 2, 3, 4, 5, 6, 7, 8, 9, 10, 11, 12, 15, 18, 21, 24, or more months.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules or cells in animal models. Various concentrations of nanoparticles in pharmaceutical composition may be administered to mice, and the minimal and maximal dosages may be determined based on the beneficial results and side effects observed as a result of the treatment. Appropriate dosage unit may also be determined by assessing the efficacy of the nanoparticle treatment in combination with other standard drugs. The dosage units of nanoparticle may be determined individually or in combination with each treatment according to the effect detected.

The pharmaceutical composition comprising the nanoparticles may be administered at appropriate intervals until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a pharmaceutical composition comprising a prodrug and/or nanoparticle of the instant invention and, preferably, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the pharmaceutical compositions of the instant invention.

The instant also encompasses delivering the nanoparticle of the instant invention to a cell in vitro (e.g., in culture). The nanoparticle may be delivered to the cell in at least one carrier.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered.

Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells and/or detectable viral levels.

As used herein, the term "prevent" refers to the prophylactic treatment of a subject who is at risk of developing a condition (e.g., HIV infection) resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a microbial infection (e.g., HIV infection) herein may refer to curing, relieving, and/or preventing the microbial infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "highly active antiretroviral therapy" (HAART) refers to HIV therapy with various combinations of therapeutics such as nucleoside reverse transcriptase inhibitors, non-nucleoside reverse transcriptase inhibitors, HIV protease inhibitors, and fusion inhibitors.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). "Hydrophobic" compounds are, for the most part, insoluble in water. As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "targeting ligand" refers to any compound which specifically binds to a specific type of tissue or cell type, particularly without substantially binding other types of tissues or cell types. Examples of targeting ligands include, without limitation: proteins, polypeptides, peptides, antibodies, antibody fragments, hormones, ligands, carbohydrates, steroids, nucleic acid molecules, and polynucleotides.

The term "aliphatic" refers to a non-aromatic hydrocarbon-based moiety. Aliphatic compounds can be acyclic (e.g., linear or branched) or cyclic moieties (e.g., alkyl and cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl," as employed herein, includes saturated or unsaturated, straight or branched chain hydrocarbons containing 1 to about 30 carbons in the normal/main chain. The hydrocarbon chain of the alkyl groups may be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). The term "lower alkyl" or "lower aliphatic" refers to an alkyl or aliphatic, respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)—$ or $NHRC(=O)—$, wherein R is an alkyl), urea ($—NHCONH_2$), alkylurea, aryl, ether, ester, thioester, nitrile, nitro, amide, carbonyl, carboxylate and thiol. Aliphatic and alkyl groups having at least about 5 carbons in the main chain are generally hydrophobic, absent extensive substitutions with hydrophilic substituents.

The following example provides illustrative methods of practicing the instant invention, and is not intended to limit the scope of the invention in any way.

Example

Preparation of Silylated Compound

To a solution of lamivudine (500 mg, 1.0 mmol) in DMF (4 mL) at 0° C., were added sequentially imidazole (222 mg, 3.271 mmol) and tert-butyldimethylsilyl chloride (TBS-Cl)

(406 mg, 2.617 mmol). The mixture was stirred and gradually warmed to room temperature over 16 hours. The mixture was then concentrated and the product was isolated by flash chromatography, eluting with 90% $CH_2Cl_2/CH_3OH$ to give the silyl ether as a colorless solid (741 mg, 99%).

Amine Protection of the Silylated Compound

To a stirred solution of the silylated compound from above (300 mg, 0.873 mmol) in anhydrous tetrahydrofuran (THF) (4 mL) at 0° C. under argon was added triethyl amine (484 μL, 3.478 mmol), then benzyl chloroformate. The mixture was stirred and gradually warmed to room temperature over 18 hours, then partitioned between ethyl acetate (30 mL) and $H_2O$ (20 mL). The aqueous layer was extracted further with ethyl acetate (4×30 mL). The organic extracts were combined, dried over $Na_2SO_4$ and concentrated. The residue was purified by flash chromatography, eluting with 70% EtOAc/Hex to give the diprotected compound (392 mg, 94%).

Hydroxyl Group Deprotection and Coupling to Fatty Acid

Tetrabutylammonium fluoride (3.4 mL, 3.4 mmol) was added dropwise to a solution of the diprotected compound (548 mg, 1.147 mmol) in THF (4 mL) at 0° C. under $N_2$. The reaction mixture was stirred and gradually warmed to room temperature for 3 hours. Calcium carbonate (1 g), Dowex-$H^+$ (3 g) and MeOH (5 mL) were then added to the reaction mixture and stirring continued for another 1 hour. The mixture was then filtered through a pad of celite, and concentrated to give the alcohol (407 mg, 98%). N,N-diisopropylethylamine (172 μL, 0.99 mmol), and 1-[bis(dimethylamino)methylene]-1H-1,2,3-triazolo[4,5-b]pyridinium 3-oxid hexafluorophosphate (HATU) (285 mg, 0.726 mmol) were added to a solution of the alcohol (120 mg, 0.33 mmol) and myristic acid (152 mg, 0.66 mmol), in DMF (4 mL) that had been stirring at 0° C. under argon. The mixture warmed to room temperature under stirring over 16 hours, concentrated, and purified by flash chromatography, eluting with 98% $CH_2Cl_2$/MeOH to give the amine protected prodrug (155 mg, 82%).

Amine Deprotection to Form the Fatty Acid Prodrug

10% Pd (15 mg) was added to a solution of the amine-protected compound from above (150 mg, 0.261 mmol) in MeOH (2 mL). The mixture was hydrogenated for 14 hours, filtered through a pad of concentrated and chromatographed with 90% $CH_2Cl_2$/MeOH to give the fatty acid prodrug (100 mg, 88%).

Preparation of ABC Prodrug

Synthesis of abacavir fatty acid prodrug was prepared by analogy to the method described for 3TC fatty acid prodrug.

Pro-Drug Encapsulation

Several antiretroviral drugs have been shown to improve patient survival. However, these drugs need to be administered on a regular basis over a prolonged period of time. Hence, the development of drug carriers that can efficiently deliver the encapsulated therapies would be a better therapeutic strategy. The present invention describes the development of long-acting nanoformulations encapsulating the synthesized potent hydrophobic pro-drugs described herein. The nanoformulations in this invention provide the advantage of high drug loading capacities, thereby diminishing overall dose burden. The following protocol illustrates how pro-drugs of the present invention can be encased into polymer excipients.

The coating polymers used were: poloxamer 407 (P407), 1,2-distearoyl-sn-glycero-3-phosphocholine (DSPC), 1,2-distearoyl-sn-glycero-3-phosphoethanolamine-N-[carboxy(polyethy lene glycol)-2000 (DSPE-PEG), and polyvinyl alcohol (PVA). 1% pro-drug was premixed with 0.5% coated polymer (P407, PEG2000, DSPC, DSPE-PEG or PVA) in HEPES buffer. Premixed suspensions were formulated by wet milling or homogenizer with the pressure of 20,000 psi, until desirable size and polydispersity index (PDI) was achieved. Dynamic light scattering (DLS) was used to detect the size, PDI and charge of the sample.

Two purification methods were used to purify the nanosuspension: 1) Homogenized suspensions were centrifuged at 500×g for 5 minutes. The supernatant was kept to remove the aggregated particles and collected supernatant was centrifuged at 20,000×g for 20 minutes to get rid of non-coated free drug and coating polymer. The pellet was collected and re-suspended in 0.1% polymer solution. 2) Homogenized suspensions could also be purified by tangential flow filtration (TFF) to remove un-coated free drug and coating polymer, which would provide formulation with well-distributed size (<200) and PDI (<0.2). Purified nano-formulations were frozen and then lyophilized.

For the cell uptake study, human monocytes were cultured and differentiated into macrophages for 7 days, and treated with cell culture medium containing 100 μM pro-drug formulation for 8 hours. At certain time points, macrophages were washed with PBS and scraped out for drug loading test by HPLC.

For the pharmacokinetic study, 6 weeks old BALB/c mice were treated with 50 mg/kg of native drug or pro-drug. Plasma was collected 1, 3, 5, 7, 10 and 14 days after administration. Tissues (liver, kidney, brain, spleen, lymph node and muscle) were collected after sacrifice on day 14. Drug and prodrug from plasma and tissues were extracted using acetonitrile and assayed by UPLC-MS/MS.

For the pre-exposure prophylaxis study, female mice were treated once either 1 week, 2 weeks, or 3 weeks prior to mating and then were euthanized one week after mating. Viral load was measured in tissues at 2, 3, or 4 weeks after drug administration.

Table 1 provides the characteristics of a 3TC prodrug formulation.

TABLE 1

3TC prodrug formulation characteristics.

| 3TC prodrug | P407 | Size | PdI | Zeta-potential | Solubility in water | Protein bind |
|---|---|---|---|---|---|---|
| 1% | 0.5% | 640 nm | 0.3 | −21 mV | 110 ng/ml | 7.0% |

The hydrophobicity of the prodrug was greatly improved upon conjugation of C12-18 alkyl groups. Prodrug solubility in water was found to be as low as 110 ng/mL, making the drug ideal for formulation. Protein binding of the prodrug was significantly improved to 7.0%; when compared to almost none for the native drug. Furthermore, the half-life of the prodrug was extended when compared to the native drug. The prodrug was successfully formulated with polymer coatings.

The nano-formulation was found to be relatively stable in PBS at 37° C. The prodrug nanoparticle release profile was found to be sustained for more than 12 days, without initial burst. The prodrug nano-formulation was effectively taken by macrophages to as high as 30 μg/million cells, which was almost 1000 times higher than the native drug (FIG. 1). The antiretroviral efficacy of the prodrug was better than that of native drug, and prodrug nano-formulation expressed long-term viral suppression capacity. The prodrug nano-formulation exhibited better antiretroviral activity than native drug as determined by reverse transcriptase activity.

Preliminary pharmacokinetic study was performed and sustained release/extended circulation time of the drug therapies was recorded in mice following administration of the prodrug loaded nanoparticles. Plasma drug level of prodrug treated mice at day 7 was 5 ng/kg, which is more than 20 times higher than in mice treated with native drug (FIG. 2).

Pre-exposure prophylaxis mice study was performed and lower risk of HIV-1 infection was tested from mice treated with prodrug formulation. The pro-drug nano-formulation effectively protected the mice from HIV-1 infection.

Targeted Formulation Development

Tissue and cell-specific antiretroviral drug delivery has received a growing amount of attention over the past few years. Intense efforts have been geared towards the development of delivery systems that would target disease reservoirs. The prodrug reservoir-targeted formulation developed in this invention offers several benefits that include increased drug levels and HIV-1 clearance in the lymphoid tissue and cellular reservoirs. The prodrug-targeted system described herein has been shown to increase the potency and efficacy of antiretroviral drugs. The protocol presented below is an example of the targeted delivery systems developed in this invention for the prodrugs.

Targeted ligand like folic acid (FA), mannose was successfully conjugated to the polymer coating. Here FA-P407 was synthesized as shown in FIG. 3. 40% of targeted polymer and 60% of non-targeted polymer was pre-mixed with the prodrug for 16 hours, under light protection. High-pressure homogenization was used to formulate the prodrug as previously described. DLS was used to detect the size, PDI and charge of the nanoparticles. The formulation can be purified by centrifugation or TFF to get desirable size and PDI. The amount of targeted ligand (FA) in the formulation was determined by the UV absorbance at 355 nm and compared against FA standard curve. Drug concentration in the purified nanosuspension was quantified by HPLC or UPLC/MS-MS. Purified nano-formulation were frozen and then lyophilized.

Particle shape was determined by scanning electron microscopy (SEM). Expression of folate receptor by macrophages was determined by Western blot and confocal microscopy (FIGS. 4 and 5). The cell uptake, pharmacokinetic, and pre-exposure prophylaxis studies were performed as described above (FIG. 6).

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A nanoparticle comprising an amphiphilic block copolymer comprising at least one block of poly(oxyethylene) and at least one block of poly(oxypropylene) coating a crystal of a compound having the formula:

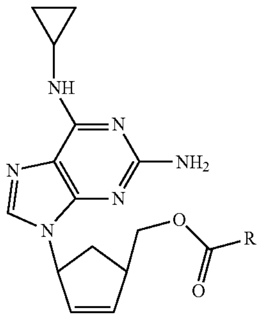

wherein R is a C4-C22 unsaturated or saturated aliphatic or alkyl chain.

2. The nanoparticle of claim 1, wherein the diameter of the nanoparticle is about 100 nm to 1 μm.

3. The nanoparticle of claim 1, wherein said amphiphilic block copolymer is poloxamer 407.

4. The nanoparticle of claim 1, wherein said nanoparticle further comprises an amphiphilic block copolymer linked to at least one targeting ligand.

5. The nanoparticle of claim 1, wherein said amphiphilic block copolymer is linked to at least one targeting ligand.

6. The nanoparticle of claim 4, wherein said targeting ligand is a macrophage targeting ligand.

7. The nanoparticle of claim 6, wherein said macrophage targeting ligand is folate.

8. The nanoparticle of claim 1, wherein said nanoparticle comprises poloxamer 407 linked to folate.

9. The nanoparticle of claim 1, wherein said R is $-(CH_2)_{12}CH_3$.

10. A nanoparticle comprising a compound having the formula:

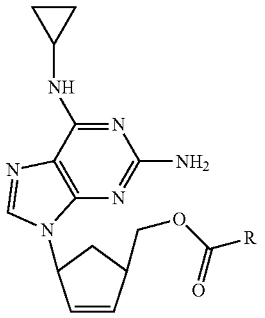

wherein R is a C4-C22 unsaturated or saturated aliphatic or alkyl chain.

11. The nanoparticle of claim 10, further comprising at least one surfactant.

12. The nanoparticle of claim 11, wherein the at least one surfactant is an amphiphilic block copolymer, polysorbate, phospholipid, derivative thereof, or combination thereof.

13. The nanoparticle of claim 11, wherein the at least one surfactant is an amphiphilic block copolymer.

14. The nanoparticle of claim 10, wherein R is $-(CH_2)_{12}CH_3$.

15. A pharmaceutical composition comprising at least one nanoparticle of claim 1 and at least one pharmaceutically acceptable carrier.

16. The pharmaceutical composition of claim 15, wherein said pharmaceutical composition further comprises an additional anti-HIV compound.

17. A pharmaceutical composition comprising at least one nanoparticle of claim 10 and at least one pharmaceutically acceptable carrier.

18. A method for treating and/or reducing the incidence of an HIV infection in a subject in need thereof, said method comprising administering to said subject a nanoparticle of claim 1.

19. The method of claim 18, further comprising the administration of an additional anti-HIV compound.

20. A method for treating or reducing the incidence of an HIV infection in a subject in need thereof, said method comprising administering to said subject a nanoparticle of claim 10.

* * * * *